United States Patent [19]

Hosoda et al.

[11] Patent Number: 4,767,660
[45] Date of Patent: Aug. 30, 1988

[54] TESTING MEMBER CAPABLE OF SELECTING A REFLECTION FACTOR

[75] Inventors: Keiji Hosoda; Masaaki Ozeki, both of Yamanashi, Japan

[73] Assignee: Hoya Corporation, Tokyo, Japan

[21] Appl. No.: 17,525

[22] Filed: Feb. 24, 1987

[30] Foreign Application Priority Data

Feb. 18, 1986 [JP] Japan ................... 61-33329

[51] Int. Cl.⁴ .......................... G01J 1/02; B32B 3/00; B44C 1/22; C23F 1/02
[52] U.S. Cl. ........................ 428/209; 156/626; 156/652; 156/653; 156/656; 156/657; 156/659.1; 156/667; 252/79.2; 356/237; 356/243; 428/432; 430/313; 430/318
[58] Field of Search ............. 156/626, 652, 653, 656, 156/657, 659.1, 661.1, 667, 345; 252/79.2; 430/5, 313, 318; 356/237, 243, 335, 336; 428/1.95, 209, 428, 432

[56] References Cited

U.S. PATENT DOCUMENTS

| | | | |
|---|---|---|---|
| 4,350,729 | 9/1982 | Nakano et al. | 428/209 |
| 4,440,841 | 4/1984 | Tabuchi | 430/05 |
| 4,512,659 | 4/1985 | Galbraith et al. | 356/243 |
| 4,530,891 | 7/1985 | Nagarekawa et al. | 430/05 |
| 4,650,744 | 3/1987 | Amano | 430/313 |

Primary Examiner—William A. Powell
Attorney, Agent, or Firm—Roberts, Spiecens & Cohen

[57] ABSTRACT

In a calibration member for use in calibrating an optical scanner, a first shading layer which is resistant against a predetermined etchant is deposited on a first principal surface of a substrate and covered with a second shading layer soluable by the predetermined etchant. The second shading layer alone is selectively etched by the predetermined etchant to leave a predetermined pattern on the first shading layer. An antireflection layer may be interposed between the first shading layer and the predetermined pattern. Alternatively, the predetermined pattern may be covered with an antireflection pattern etched together with the second shading layer. Similar structure may be formed on a second principal surface of the substrate.

10 Claims, 4 Drawing Sheets

TESTING MEMBER CAPABLE OF SELECTING A REFLECTION FACTOR

BACKGROUND OF THE INVENTION

This invention relates to a testing device for testing a measuring device. In particular, this invention relates to a calibration member for use in calibrating an optical scanner before the optical scanner is used for detection of foreign particles or flaws on a surface of a substrate and to a method of manufacturing the calibration member.

On manufacturing a semiconductor integrated circuit, a semiconductor substrate is used to form a wide variety of circuit elements. At any rate, the semiconductor substrate should have a clean principal surface. In other words, any foreign particles, such as dust or dirt, and flaws must be removed from the principal surface so as to manufacture the circuit elements having desired characteristics. Therefore, it is necessary that such foreign particles and flaws are measured and detected with high sensitivity on the principal surface of each semiconductor substrate.

An optical scanner is used to measure sizes of the foreign particles and the flaws and comprises an optical scanning portion for scanning the principal surface by a laser beam and a photodetector for detecting light reflected and scattered on the principal surface of the semiconductor substrate. However, it is to be noted here that each optical scanner might have sensitivity variable in dependency upon an optical characteristic of each photodetector and upon an atmospheric condition of measurement.

Under the circumstances, each optical scanner must be calibrated to determine the sensitivity before the foreign particles and/or flaws are measured in connection with the semiconductor substrate. Calibration is carried out by the use of a calibration member which has standard patterns of desired sizes and thicknesses. The standard patterns may be called dummy foreign particles or dummy patterns because they are formed instead of the foreign particles on the semiconductor substrate.

A conventional calibration member has the dummy patterns which are formed by etching a semiconductor wafer on a wafer surface by the use of a photolithographic technique. It is mentioned here that an etch rate is liable to be varied, depending upon an etching time, concentration and temperature of an etchant, and the like. Accordingly, it is difficult to adjust the thicknesses of the dummy patterns of each calibration member to the desired thickness. This shows that the dummy patterns of each calibration member may be different in thickness from those of the other calibration members. As a result, such differences of thicknesses of the dummy patterns make it difficult to accurately calibrate the optical scanner.

In the U.S. Pat. No. 4,512,659, a calibration member is revealed by Galbraith et al to calibrate the optical scanner and comprises a semiconductor wafer coated with a thin layer of oxide or nitride. The thin layer is partially removed to form the dummy patterns. The thicknesses of the dummy patterns may be adjusted to a desired thickness in each calibration member.

In the meanwhile, such a calibration member might be applied not only to calibration of a semiconductor device but also to calibration of a photomask or a photomask blank. On application of the above-mentioned conventional calibration member to calibration of the photomask or photomask blank, inconvenience takes place because light scattered from the photomask or photomask blank is noticeably different from that scattered from the semiconductor device.

In addition, the conventional calibration member is expensive because of use of a refined semiconductor wafer.

SUMMARY OF THE INVENTION

It is an object of this invention to provide a calibration member which is suitable for calibrating not only a semiconductor device but also a photomask or a photomask blank.

It is another object of this invention to provide a calibration member of the type described, which is inexpensive in comparison with a conventional calibration member.

It is a further object of this invention to provide a calibration member of the type described, wherein thicknesses of dummy patterns can be adjusted to a desired thickness.

It is a still another object of this invention to provide a method of manufacturing a calibration member, wherein thicknesses of dummy patterns can be readily adjusted to a desired thickness.

According to this invention, a calibration member comprises a substrate having a first principal surface, a first shading layer which is adjacent to the first principal surface and which is resistant against a predetermined etchant, and a predetermined pattern farther from the first principal surface than the first shading layer and formed from a second shading layer which is not resistant against the predetermined etchant.

DESCRIPTION OF THE PREFERRED EMBODIMENTS

Figure 1:
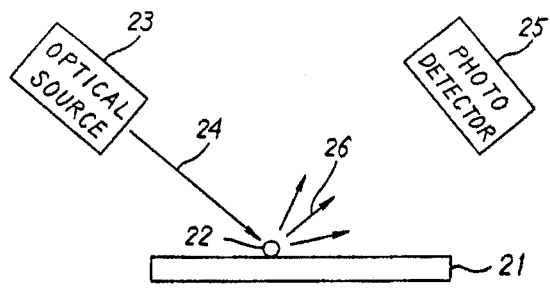
FIG. 1 shows a schematic view for use in describing operation of an optical scanner which is calibrated by the use of a calibration member.

Referring to FIG. 1, description will be made as regards a method of testing a substrate 21 by the use of an optical scanner to detect foreign particles 22 on the substrate 21. Such an optical scanner comprises an optical source 23 for emitting a laser beam 24 onto the substrate 21 and a photodetector 25 for detecting light 26 scattered from the foreign particles 22. The laser beam 24 may have a wavelength between 400 nm and 700 nm.

It is assumed that the optical scanner is already calibrated by the use of a calibration member to which this invention is applicable. As a result, the optical scanner is assumed to have known sensitivity. Under the circumstances, sizes of the foreign particles 22 can be measured by the optical scanner because an amount of the scattered light 26 can be made to correspond to the sizes of the foreign particles 22, as known in the art. For example, when the foreign particles 22 are spherical dust particles of 1 micron meter in diameter, the photodetector 25 produces, as a detection signal, an electric signal having an amplitude or power corresponding to sizes of the spherical dust particles. From this fact, it is readily understood that the optical scanner must be previously accurately calibrated by the use of the calibration member so as to take an accurate measurement of the sizes of the foreign particles 22.

In addition, the photodetector 25 also receives light reflected from a substrate surface of the substrate 21. Therefore, a result of measurement is variable depending on an amount of the reflected light from the substrate surface.

Figure 2:
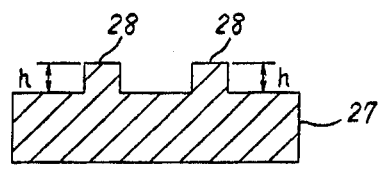
FIG. 2 shows a sectional view of a conventional calibration member.
Figure 3:
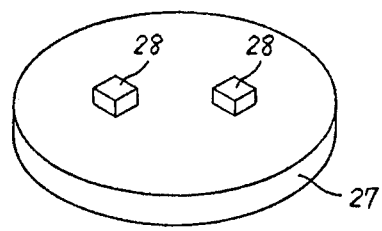
FIG. 3 shows a perspective view of the conventional calibration member illustrated in FIG. 2.

Referring to FIGS. 2 and 3, description will be made as regards a conventional calibration member for a better understanding of this invention. The conventional calibration member is for use in calibrating a semiconductor device and is implemented by a silicon wafer 27 having dummy patterns or dummy foreign particles 28 formed on a wafer surface. The dummy patterns 28 serve to simulate foreign particles on the substrate, such as 21, and have a predetermined size. The dummy patterns 28 may be composed of a plurality of partial patterns which are different in size from one another.

The dummy patterns 28 can be formed by a usual photolithographic technique. More specifically, a photoresist layer is deposited on a wafer surface of the silicon wafer 27 and subjected to exposure and selective removal. Thereafter, the silicon wafer 27 is etched by the use of an etchant with the photoresist layer partially removed on the wafer surface. Thus, the dummy patterns 28 are left by directly etching the silicon wafer 27.

Herein, an etch rate is varied in dependency upon an etching condition, as mentioned in the preamble of the instant specification. Therefore, it is difficult to adjust heights h of the dummy patterns 28 to a predetermined height. This shows that the heights h of the dummy patterns 28 of each calibration member are different from one another.

The conventional calibration member is suitable for calibrating the optical scanner when the optical scanner used for measuring a semiconductor device comprising a silicon wafer.

On the other hand, it is a recent trend that such a calibration member is also used when a photomask or a photomask blank is measured by the optical scanner. In this event, the conventional calibration member may be unsuitable because light reflected from a wafer surface of the photomask or photomask blank is different from the light reflected from the wafer surface of the silicon wafer.

Figure 4:
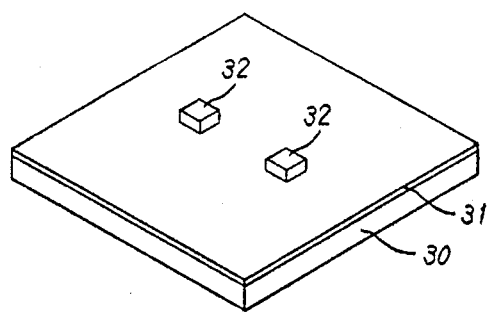
FIG. 4 shows a perspective view of a calibration member according to a first embodiment of this invention.

Referring to FIG. 4, a calibration member according to a first embodiment of this invention comprises a substrate 30 of soda-lime glass having a first principal surface directed upwards of FIG. 4 and a second principal surface opposite to the first principal surface. The substrate 30 is rectangular in shape, as shown in FIG. 4, and is, for example, 5 in. × 5 in. × 0.09 in. The substrate 30 is transparent to a laser beam having a wavelength between 400 nm and 700 nm.

On the first principal surface of the substrate 30, a first shading layer 31 is deposited to a thickness of 600 angstroms by sputtering. The first shading layer 31 serves to shade the above-mentioned laser beam and is resistant against a predetermined etchant. The predetermined etchant may be, for instance, a mixed solution of ceric ammonium nitrate and perchloric acid. Therefore, the first shading layer 31 may be formed, for example, by titanium.

A second shading layer is deposited to a thickness of 1000 angstroms by sputtering on the first shading layer 31 and is etched into a plurality of dummy patterns 32 which may be called dummy foreign particles or standard patterns. The illustrated second shading layer is brought into contact with the first shading layer 31 and serves to shade the laser beam like the first shading layer 31. However, it is to be noted that the second shading layer is not resistant against the predetermined etchant. In other words, the second shading layer is soluable in the predetermined etchant and may be formed by chromium in the example being illustrated in FIG. 4.

From this fact, it is to be understood that the second shading layer alone is etched by the predetermined etchant while the first shading layer 31 is not etched by the predetermined etchant. Empirically, it has been confirmed that a deposit rate can accurately be controlled on depositing each of the first and the second shading layers. Accordingly, it is readily possible to adjust the thickness or height of the dummy patterns 32 to a predetermined thickness of, for example, 1000 angstroms.

Referring to FIGS. 5(a) through 5(e) together with FIG. 4, description will be made about a method of manufacturing the calibration member illustrated in FIG. 4. In FIG. 5(a), the substrate 30 is at first prepared by cutting a glass plate of soda-lime glass into a plurality of glass pieces, by polishing both principal surfaces of each glass piece, by cleaning or washing each piece in pure water, isopropyl alcohol, and the like, and by drying each washed piece. Thereafter, the first shading layer 31 of titanium is deposited on the first principal surface to the thickness of 600 angstroms by sputtering. On the first shading layer 31, the second shading layer (depicted at 32a in FIG. 5(a)) of chromium is deposited to the thickness of 1000 angstroms by sputtering. Subsequently, a photoresist layer 33 is coated on the second shading layer 32a by spin coating to a thickness of 5000 angstroms. The photoresist layer 33 may be of a positive-working photoresist, namely, a photoresist of a positive type, which may be MP-1350 manufactured and sold by Shipley Company Incorporated.

As illustrated in FIG. 5(b), the photoresist layer 33 is exposed through a photomask or exposure mask 34 by an ultraviolet ray 35 of a wavelength between 200 nm and 450 nm. Transparent portions of the photomask 34 are symbolized by non-hatched portions while opaque portions thereof are symbolized by hatched portions for convenience of illustration.

Subsequently, the photoresist layer 33 is selectively removed by the use of a predetermined developer at portions of the photoresist layer 33 which are exposed through the transparent portions of the photomask 34. As a result, unexposed portions of the photoresist layer 33 are left as a resist pattern on the second shading layer 32a, as shown in FIG. 5(c).

Under the circumstances, the second shading layer 32a is etched by the predetermined etchant, such as the mixed solution of the ceric ammomium nitrate and perchloric acid, into the dummy patterns 32, as shown in FIG. 5(d). In this case, the first shading layer 31 is not etched by the predetermined etchant at all. Such etching is carried out during an etching time which may be slightly longer than a just etching time of 40 seconds and which may be, for example, 50 seconds.

As shown in FIG. 5(e), the resist pattern 36 is peeled off by the use of a peeling solvent, such as concentrated sulfuric acid heated to a temperature of 90° C. Thereafter, a combination of the substrate 30, the first shading layer 31, and the dummy patterns 32 is immersed into sulfuric acid of a room temperature to be cooled and is subjected to ultrasonic cleaning within water and isopropyl alcohol and is thereafter dried within Freon gas. In consequence, the calibration member is obtained which comprises the dummy patterns 32 remaining on the first shading layer 31, as illustrated in FIG. 5(e).

As mentioned before, etching of the second shading layer 32a may be carried out until the first shading layer 31 is exposed because the first shading layer 31 is resistant against the predetermined etchant which is selected to etch the second shading layer 32a. In other words, etching may last during the etching time which is equal to or longer than the just etching time. This means that the dummy patterns 32 are formed with a high precision even when strict control is not made about etching conditions, such as concentration and temperature of the predetermined etchant and the etching time. Anyway, it is readily possible with this method to adjust the height or thickness of the dummy patterns 32 to a predetermined height $h_1$. The thickness of the dummy patterns 32 is substantially equal to the thickness of the second shading layer 32a while two-dimensional sizes, namely, lengths and widths of the dummy patterns 32 are substantially determined by the photomask 34.

Figure 5:
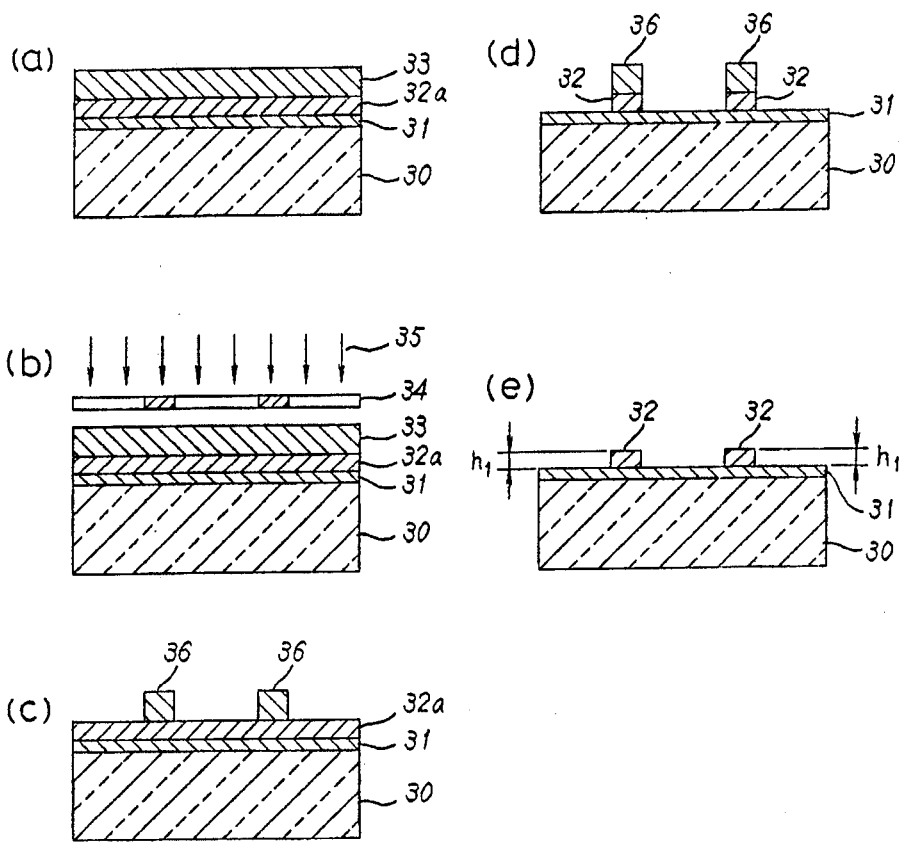
FIG. 5(a) through 5(e) shows sectional views for use in describing processes of manufacturing the calibration member illustrated in FIG. 4.
Figure 6:
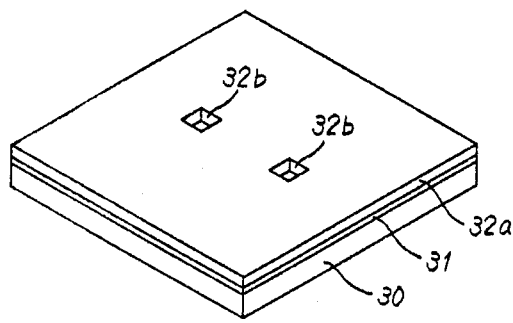
FIG. 6 shows a perspective view of a calibration member according to a second embodiment of this invention.
Figure 7:
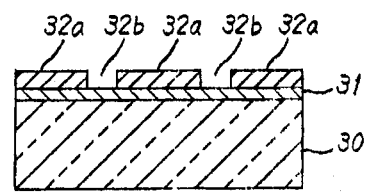
FIG. 7 shows a sectional view of the calibration member illustrated in FIG. 6.

Referring to FIGS. 6 and 7, a calibration member according to a second embodiment of this invention is similar to that illustrated in FIGS. 4 and 5 except that dummy patterns 32b are provided by depressions formed in the second shading layer 32a. The illustrated calibration member can simulate flaws and/or foreign particles on a substrate, such as a photomask or a photomask blank. In this case, the second shading layer 32a are partially etched to form the depressions and are almost left on the first shading layer 31. In other words, the dummy patterns 32b are surrounded by the second shading layer 32a.

Figure 8:
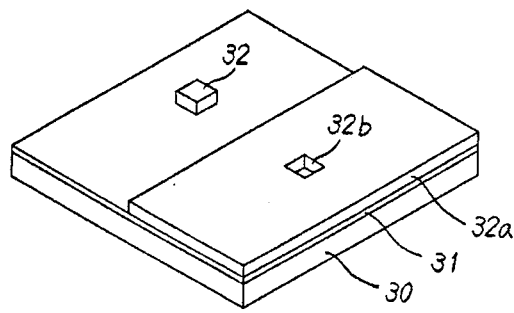
FIG. 8 shows a perspective view of a calibration member according to a third embodiment of this invention.
Figure 9:
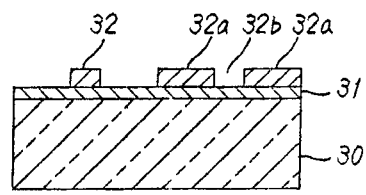
FIG. 9 shows a sectional view of a calibration member illustrated in FIG. 8.

Referring to FIGS. 8 and 9, a calibration member according to a third embodiment of this invention is substantially equivalent to a combination of the calibration member illustrated in FIGS. 4 and 5 and the other calibration member illustrated in FIGS. 6 and 7. More particularly, the calibration member shown in FIGS. 8 and 9 is divisible into two areas one of which has, as the dummy pattern 32, a projection formed in the manner described with reference to FIGS. 4 and 5 and the other of which has, as the other dummy pattern 32b, a depression formed in the manner described in conjunction with FIGS. 6 and 7. At any rate, the projection and the depression may be formed by etching the second shading layer 32a.

Such a calibration member can be manufactured in the following manner. The photoresist layer of the positive type is exposed and developed in the manner shown in FIG. 5(b) by the use of a photomask having shading patterns and transparent portions corresponding to the dummy patterns 32 and 32b. Thereafter, the second shading layer 32a is etched into the dummy patterns 32 and 32b.

Alternatively, each of the dummy patterns 32 and 32b may individually be formed by partially and successively coating a photoresist layer on each area and by separately etching each photoresist layer.

Figure 10:
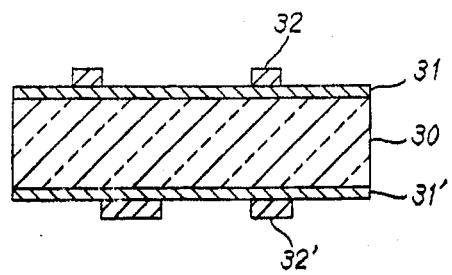
FIG. 10 shows a sectional view of a calibration member according to a fourth embodiment of this invention.

Referring to FIG. 10, a calibration member according to a fourth embodiment of this invention comprises a first shading layer 31 on a first one of principal surfaces of a substrate 30 and a dummy pattern 32 on the first shading layer 31, like in FIGS. 4 through 9. The dummy pattern 32 may be formed in the manner described in conjunction with FIGS. 4 through 9 and will be referred to as a first dummy pattern.

As shown in FIG. 10, the illustrated calibration member comprises an additional shading layer 31' on a second one of the principal surfaces of the substrate 30 and an additional dummy pattern 32' on the additional shading layer 31'. The additional shading layer 31' may be composed of the same material as the first shading layer 31. On the other hand, the additional dummy pattern 32' may be composed of the same material as the second shading layer 32a shown in FIGS. 4 through 9 and is formed in the manner described with reference to FIGS. 4 through 9. The additional dummy pattern 32' will be called a second dummy pattern.

With this structure, the first and the second dummy patterns 32 and 32' may have patterns different from each other. Therefore, the illustrated calibration member can simulate different sizes of foreign particles by the first and the second dummy patterns 32 and 32' formed on both principal surfaces of the substrate 30.

Figure 11:
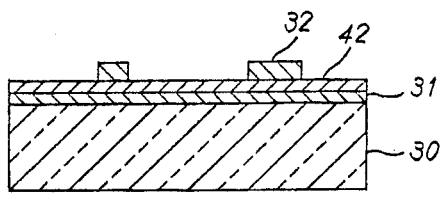
FIG. 11 shows a sectional view of a calibration member according to a fifth embodiment of this invention.

Referring to FIG. 11, a calibration member according to a fifth embodiment of this invention is similar to that illustrated in FIGS. 4 and 5 except that an intermediate layer 42 is interposed between the first shading layer 31 of titanium and the dummy pattern 32 of chromium so as to avoid reflection of the laser beam (FIG. 1) on the intermediate layer 42. Therefore, the intermediate layer 42 has a low reflection factor in comparison with the dummy pattern 32 and serves as an antireflection layer and may be of titanium oxide. The dummy pattern 32 is brought into contact with the intermediate layer 42 and partially left on the intermediate layer 42 with the intermediate layer 42 partly uncovered.

In FIG. 11, let the laser beam be incident onto exposed portions of the intermediate layer 42. In this event, the laser beam is rarely reflected by the intermediate layer 42, which makes reflection light weak. As a result, the photodetector 25 (FIG. 1) produces the detection signal including a reduced noise signal when the dummy pattern 32 is scanned by the laser beam. Thus, it is possible to confirm intensity of light scattered from the dummy pattern 32 with reference to a result of scanning the exposed portions of the intermediate layer 42.

The intermediate layer 42 may not always be an antireflection layer.

Figure 12:
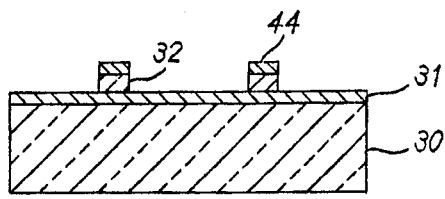
FIG. 12 shows a sectional view of a calibration member according to a sixth embodiment of this invention.

Referring to FIG. 12, a calibration member according to a sixth embodiment of this invention is similar to that illustrated in FIGS. 4 and 5 except that each of the dummy patterns 32 of chromium is covered with an overlying pattern 44 of chromium oxide. As shown in FIG. 12, the overlying pattern 44 is formed by etching a chromium oxide layer together with the second shading layer 32a (FIG. 5).

Alternatively, the overlying layer 44 may be either an antireflection layer or a shading layer similar to the first and the second shading layers mentioned above.

In the examples being illustrated in FIGS. 4 through 12, a marker may be formed along a peripheral portion of each calibration member to discriminate each calibration member. For this purpose, the peripheral portion of each calibration member is partially etched to expose the substrate 30.

Although titanium and chromium are exemplified as materials of the first and the second shading layers 31 and 32a, respectively, each of the first and the second shading layers may comprise a material selected from a group consisting of components, such as chromium, titanium, aluminum, silicon, tungsten, tantalum, molybdenum, and the like and oxides, nitrides, carbides, and silicides of the above-mentioned components. For example, the first shading layer 31 may comprise titanium oxide, titanium nitride, or titanium carbide in order to make a reflection factor differ from the first shading layer comprising titanium.

In the above-mentioned embodiments, the glass plate of soda-lime glass is used as the substrate 30. However, the substrate 30 may be of aluminosilicate glass, quartz, ceramics, aluminum, silicon, or the like. At any rate, the first and the second shading layers 31 and 32a are formed on the substrate 30 with the second shading layer 32a alone etched into the dummy patterns 32. With this structure, a wide variety of materials can be used as the first shading layer 31. This means that the reflection factor of the first shading layer 31 can be selected in consideration of each reflection factor of test substrates which are to be tested by the optical scanner and that accurate calibration of the optical scanner can be carried out by the use of the calibration member according to this invention.

More particularly, it is possible to render the reflection factor of the first shading layer 31 equal to that of the test substrates to be tested. Such equality between the reflection factors of the first shading layer 31 and the test substrates enables simulation of that surface of each test substrate which has no foreign particle or no flaw. Therefore, when exposed portions of the first shading layer 31 are scanned by the laser beam, a noise signal which is produced from the photodetector 25 is substantially equal in amplitude to a noise signal appearing from the test substrates having no foreign particles. Thus, calibration of the optical scanner can favorably be carried out by the use of the calibration member.

While this invention has thus far been described in conjunction with several embodiments thereof, it will readily be possible for those skilled in the art to put this invention into practice in various other manners. For example, an additional underlying layer may be laid between the first principal surface of the substrate 30 and the first shading layer 31 and may be different from the first shading layer 31. The dummy patterns 32 may have optional configurations of, for example, squares, rectangles, polygons, circles, and the like, and may have optional sizes determined for measuring sensitivity. Each of the first and the second shading layers 31 and 32a may be deposited by chemical vapor deposition, vacuum evaporation, or ion plating.

The photoresist may be a negative-working photoresist or may be replaced by an electron beam resist of a positive type or a negative one. Such a resist may be coated by roll coating and etched by an etchant determined for etching the second shading layer 32a with the first shading layer 31 unetched. Such etching is not restricted to wet etching but may be dry etching, such as sputter etching, plasma etching, or the like.

What is claimed is:

1. A calibration member comprising:
    a substrate having a first principal surface;
    a first shading layer which is adjacent to said first principal surface and which is resistant against a predetermined etchant; and
    a predetermined pattern farther from said first principal surface than said first shading layer and formed from a second shading layer which is not resistant against said predetermined etchant.

2. A calibration member as claimed in claim 1, further comprising;
    an additional layer between said first principal surface and said first shading layer.

3. A calibration member as claimed in claim 1, wherein said first shading layer is deposited on and brought into contact with said first principal surface.

4. A calibration member as claimed in claim 3, wherein said predetermined pattern is deposited on and brought into contact with said first shading layer.

5. A calibration member as claimed in claim 4, said substrate having a second principal surface opposite to said first principal surface, said calibration member further comprising:
    an additional shading layer which is deposited on said second principal surface and which is resistant against said predetermined etchant; and
    an additional pattern which is deposited on said additional shading layer and which is not resistant against said predetermined etchant.

6. A calibration member as claimed in claim 3, further comprising:
    an antireflection layer between said first shading layer and said predetermined pattern.

7. A calibration member as claimed in claim 1, wherein said predetermined pattern is deposited on and brought into contact with said first shading layer.

8. A calibration member as claimed in claim 7, further comprising:
    an overlying pattern on said predetermined pattern.

9. A method of manufacturing a calibration member, said method comprising the steps of:
    preparing a substrate having a first principal surface and a second principal surface opposite to said first principal surface;
    depositing on said first principal surface a first shading layer which is resistant against a predetermined etchant;
    depositing on said first shading layer a second shading layer which is not resistant against said predetermined etchant; and selectively removing only said second shading layer by said predetermined etchant to leave a predetermined pattern on said first shading layer.

10. A method as claimed in claim 9, wherein said selectively removing step comprises the steps of:
coating a resist on said second shading layer;
exposing said resist through a photomask to form exposed portions and unexposed portions in said resist;
eliminating preselected ones of said exposed and unexposed portions; and
selectively etching said second shading layer at portions corresponding to said preselected ones of the exposed and the unexposed portions of said resist.

* * * * *